United States Patent
Zhao et al.

(10) Patent No.: US 10,240,048 B2
(45) Date of Patent: Mar. 26, 2019

(54) CORROSION-INHIBITING MICROGELS AND NON-CHROMATED PRIMER COMPOSITIONS INCORPORATING THE SAME

(71) Applicant: Cytec Industries Inc., Woodland Park, NJ (US)

(72) Inventors: Yiqiang Zhao, Newark, DE (US); Dalip Kohli, Churchville, MD (US); Keltoum Ouzineb, Lyons (FR)

(73) Assignee: CYTEC INDUSTRIES INC., Woodland Park, NJ (US)

( * ) Notice: Subject to any disclaimer, the term of this patent is extended or adjusted under 35 U.S.C. 154(b) by 896 days.

(21) Appl. No.: 14/132,547

(22) Filed: Dec. 18, 2013

(65) Prior Publication Data

US 2014/0187672 A1    Jul. 3, 2014

Related U.S. Application Data

(60) Provisional application No. 61/746,675, filed on Dec. 28, 2012.

(51) Int. Cl.
*C09D 5/08*    (2006.01)
*C08K 9/12*    (2006.01)
(Continued)

(52) U.S. Cl.
CPC .......... *C09D 5/086* (2013.01); *C07D 235/28* (2013.01); *C07D 249/18* (2013.01); *C07D 277/82* (2013.01); *C07D 403/12* (2013.01); *C08F 236/00* (2013.01); *C08G 59/08* (2013.01); *C08G 59/56* (2013.01); *C08K 5/3475* (2013.01);
(Continued)

(58) Field of Classification Search
CPC .......... C09D 5/08; C09D 5/082; C09D 5/086; C09D 163/00–163/10; C09D 147/00; C08K 9/10; C08K 9/12; C08K 5/3475; C08K 5/47; C08L 63/00–63/10; C08L 47/00; C08F 236/00; C08F 236/02;
(Continued)

(56) References Cited

U.S. PATENT DOCUMENTS 5,574,377 A * 11/1996 Marquez-Lucero ........................ G01M 3/045
174/11 R
6,075,072 A   6/2000 Guilbert et al.
(Continued)

FOREIGN PATENT DOCUMENTS

EP    1832629 A1    9/2007
WO   9914277 A1    3/1999
(Continued)

OTHER PUBLICATIONS

Seiffert S., Thiele, J. et al., "Smart Microgel Capsules from Macromolecular Precursors", J. Am. Chem. Soc. 2010, 132, 6606-6609.
(Continued)

Primary Examiner — Kregg T Brooks
(74) Attorney, Agent, or Firm — Thi Dang

(57) ABSTRACT

Corrosion-inhibiting microgels that are suitable for use in non-chromated primer compositions. Each discrete microgel is composed of a cross-linked polymer network and organic corrosion-inhibiting compounds entrapped or immobilized within the polymer network.

15 Claims, 1 Drawing Sheet

(51) Int. Cl.
*C08F 236/00* (2006.01)
*C09D 147/00* (2006.01)
*C08K 5/47* (2006.01)
*C08K 5/3475* (2006.01)
*C07D 277/82* (2006.01)
*C07D 403/12* (2006.01)
*C07D 249/18* (2006.01)
*C07D 235/28* (2006.01)
*C08G 59/08* (2006.01)
*C08G 59/56* (2006.01)
*C08G 59/20* (2006.01)
*C08F 220/18* (2006.01)
*C08L 33/06* (2006.01)
*C23F 11/00* (2006.01)
*C09D 163/00* (2006.01)

(52) U.S. Cl.
CPC ............... *C08K 5/47* (2013.01); *C08K 9/12* (2013.01); *C09D 5/08* (2013.01); *C09D 5/082* (2013.01); *C09D 147/00* (2013.01); *C09D 163/00* (2013.01)

(58) Field of Classification Search
CPC ... C08F 236/22; C07D 235/28; C07D 249/18; C07D 277/82; C07D 403/12
See application file for complete search history.

(56) References Cited

U.S. PATENT DOCUMENTS

| 6,284,843 | B1* | 9/2001 | Jariwala ............... C07C 323/52 264/211.12 |
| 6,387,497 | B1 | 5/2002 | Nishida et al. |
| 6,436,508 | B1* | 8/2002 | Ciammaichella et al. ... 428/131 |
| 6,933,046 | B1 | 8/2005 | Cook |
| 2004/0104378 | A1 | 6/2004 | Bhatia |
| 2006/0275966 | A1* | 12/2006 | Park ........................ H01J 9/025 438/182 |
| 2008/0254133 | A1* | 10/2008 | Saunders ................ A61L 27/16 424/501 |
| 2010/0247922 | A1 | 9/2010 | Shah et al. |
| 2013/0017612 | A1* | 1/2013 | Li ............................ C09D 5/08 436/75 |
| 2013/0196173 | A1* | 8/2013 | Park ........................ B01J 13/22 428/623 |

FOREIGN PATENT DOCUMENTS

| WO | 02/22744 A2 | 3/2002 |
| WO | 2010/117757 A1 | 10/2010 |
| WO | 2011/126165 A1 | 10/2011 |

OTHER PUBLICATIONS

Sebastian B., Rekha S., et al., "Microgel/Clay Nanohybrids as Responsive Scavenger Systems", Polymer, 2010, 51, 3829-3835.

Alexandra Latnikove et al. A new approach towards "Active" self-healing coatings: exploitation of microgels, Soft Matter, vol. 8, No. 42, Sep. 3, 2012.

International Search Report. PCT/US2013/075910, dated Mar. 27, 2014.

Yang Yuxia et al., "Preparation of Polyacrylic Acid Type Hydrogel and Its pH Sensitive Behavior in Alkaline Solution," Chinese Journal of Material Research, vol. 26, No. 1, pp. 85-90.

* cited by examiner

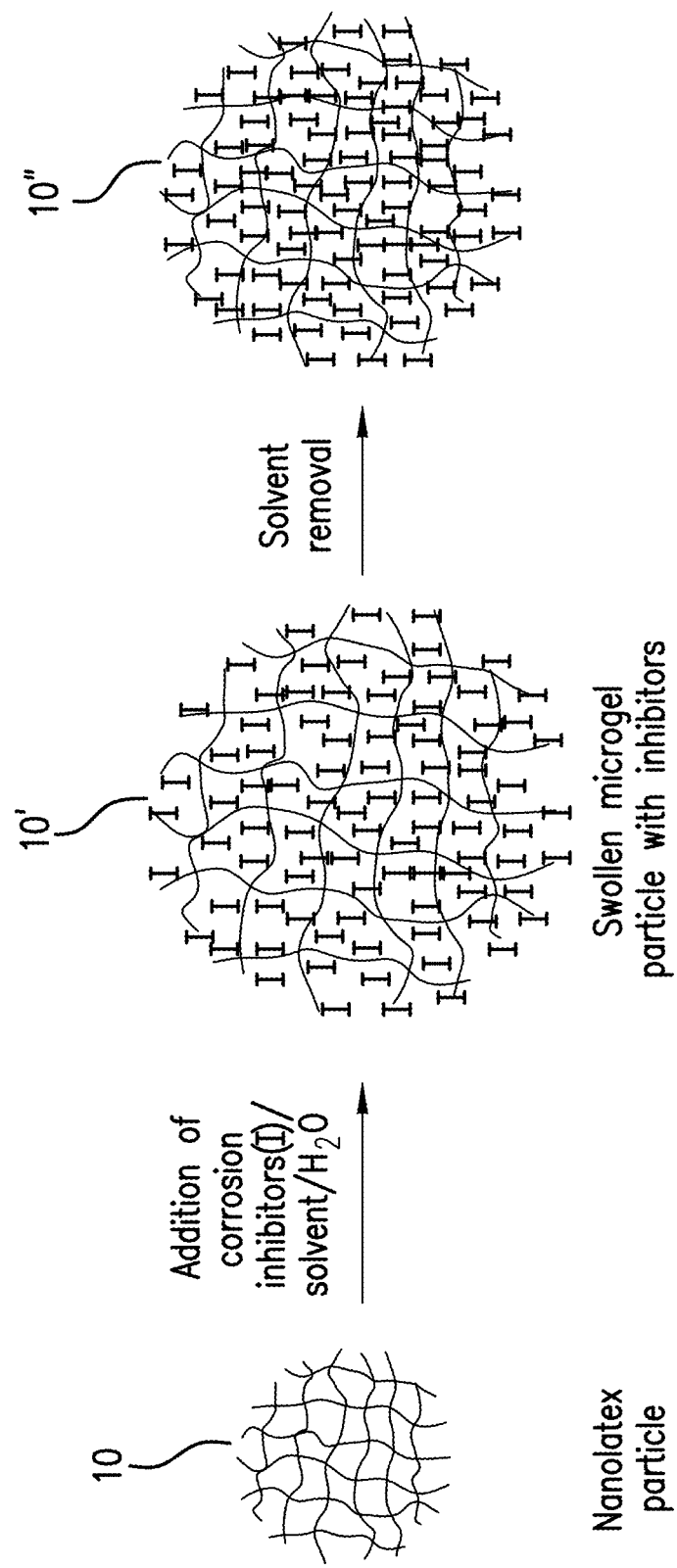

CORROSION-INHIBITING MICROGELS AND NON-CHROMATED PRIMER COMPOSITIONS INCORPORATING THE SAME

This application claims the benefit of U.S. Provisional Patent Application No. 61/746,675, filed Dec. 28, 2012, the disclosure of which is incorporated by reference in its entirety.

BACKGROUND

In the manufacture of composite structures, it is conventional to bond a metallic structure to another metal structure or to a composite structure composed of resin impregnated fibrous reinforcement utilizing structural adhesives. In general, to ensure the greatest level of adhesive strength, the metal surface(s) are scrupulously cleaned of dirt, soil, grease, and metal oxidation products immediately prior to bonding. Unfortunately, this procedure cannot be generally used most times, as the cleaning and bonding operations are often separated by long periods of time. During such periods, the metal surface may become hydrolyzed, lessening the adhesive strength of the bond. One alternative to overcome this difficulty is to use a primer on the cleaned metal surface.

Historically, chromated primers (i.e., solutions containing chromium ions) have been used to protect metals from corrosion. However, due to environmental regulations, the use of chromates is restricted, particularly in the aerospace industry, among others. Several non-chromated corrosion inhibitors such as zinc phosphosilicates, molybdenum zinc phosphate, calcium borosilicate, sodium vanadate, strontium phosphate etc. have been under evaluation. Most of these inhibitors are passive (cannot leach-like chromates) and provide corrosion protection by sacrificial oxidation method. As such, these passive inhibitors do not provide the desired durability or performance required when exposed to harsh environmental conditions.

Some conventional organic corrosion inhibitors rely on a mechanism through which organic species prevent corrosion is by reacting with the metal substrate, the oxide film or the corrosion products to form an adherent film to prevent further corrosion. A major drawback of these organic corrosion inhibitors relates to the interaction of the functional groups used to form strong adherent bonds on a metal substrate with the primer formulation. Due to this interaction, the shelf life and cure kinetics of the primer may be affected, which limits corrosion inhibitor transport within a coating to the corrosion site. Another drawback with many organic corrosion inhibitors is their unpredictable corrosion performance when used with epoxy based corrosion inhibiting primer formulations in preventing corrosion on highly corrosive material such as aluminum and aluminum alloys.

Therefore, there remains a need for non-chromated primer formulations that can perform similarly to chromate corrosion inhibitors for structural bonding applications, particularly in industries such as aerospace and automotive.

SUMMARY

Disclosed herein is a microgel corrosion inhibiting material for use in a water-based, non-chromated (i.e., chromate-free) primer composition. Such non-chromated primer composition is particularly suitable for structural bonding applications and can meet the environmental regulations that limit the use of chromates.

BRIEF DESCRIPTION OF THE DRAWINGS

FIG. 1 schematically illustrates a method of preparing a corrosion-inhibiting microgel according to an embodiment.

DETAILED DESCRIPTION

The corrosion inhibiting microgels of the present disclosure are discrete, cross-linked polymer particles of nanometer or sub-micron sizes. Each discrete microgel is composed of a cross-linked polymer network having corrosion inhibitor compounds entrapped or immobilized within the polymer network. The corrosion inhibitor compounds are releasable from the cross-linked polymer networks upon exposure to corrosion-triggering conditions such as pH change, moisture exposure and temperature increase.

The corrosion inhibiting microgels disclosed herein may be prepared by the following method:
a) Forming discrete microgels by emulsion polymerization of monomers in a liquid medium;
b) Dissolving an organic corrosion inhibitor in an aqueous medium containing an organic solvent and water;
c) Mixing the microgels with the aqueous medium, causing the microgels to swell and the organic corrosion inhibitor compounds to become entrapped or immobilized within the polymer networks; and
d) Stripping off the solvent to produce a latex emulsion with microgels of smaller particle sizes and increased solid content.

FIG. 1 schematically illustrates the method for forming a microgel particle loaded with corrosion inhibiting compounds. Referring to FIG. 1, a discrete, untreated microgel particle 10 is exposed to an aqueous medium containing corrosion inhibitors, solvent and water, resulting in a swollen microgel 10' loaded with corrosion inhibiting compounds "I", and after solvent removal, a shrunken, corrosion-inhibiting microgel particle 10" is produced.

Microgels are discrete, spheroidal polymeric particles having micron, submicron or nanometer size, and are composed of cross-linked polymer network. Microgels may also be referred to as nano-sponges due to their capability to swell and shrink (i.e. de-swell) upon external conditions, enabling the encapsulation of substances and release of the same in a controllable manner. Microgels are prepared via polymerization of monomers in a specific liquid medium. Typically, emulsion polymerization, either water-in-oil or oil-in-water type, is employed to prepare microgel particles in latex form. Here, the emulsion polymerization for forming microgels includes several sub-category types such as micro-emulsion, mini-emulsion, emulsifier-free, seeded emulsion polymerization and so on. In general, other polymerization in liquid media such as dispersion polymerization and suspension polymerization may also be employed to make microgel particles having nanometer to millimeter sizes. Post-emulsification of bulk polymer or polymer solutions may also produce microgels with the addition of emulsifiers or surfactants.

The monomers used in the polymerization to make microgels include mono-functional acrylic and methacrylic monomers such as ethyl acrylate (EA), methyl methacrylate (MMA), benzyl acrylate, benzyl methacrylate, butyl acrylates, butyl methacrylate, propyl acrylates, propyl methacrylate, cyclohexyl acrylates, cyclohexyl methacrylate, decyl acrylates, decyl methacrylate, dodecyl acrylates, dodecyl methacrylate, octyl methacrylate, methoxyethyl acrylate, methoxyethyl methacrylate, etc.; bi-functional acrylic and methacrylic monomers such as methyl methacrylic acid (MAA), acrylic acid (AA), acrylates and methacrylates containing hydroxyl group such as hydroxyethyl methacrylate and hydroxyethyl acrylate, acrylates and methacrylates containing primary/secondary/tertiary amino group, acrylamides and their derivatives, methacrylamides and their derivatives, etc.; mono-functional vinyl monomers such as styrene and its derivatives, vinyl acetate and its derivatives etc.

The monomers used in the polymerization to make microgels also include multi-functional cross-linking monomers selected from, but are not limited to, diacrylates and dimethacrylates such as ethylene glycol diacrylate, diethylene glycol dimethacrylate (EGDMA), tetraethylene glycol dimethacrylate, etc; triacrylates and trimethacrylates such as trimethylolpropane trimethacrylate (TMPTMA), pentaerythritol triacrylate, etc.; dipentaerythritol pentaacrylate, pentaerythritol tetraacrylate; other difunctional crosslinking monomers such as divinylbenzene (DVB), derivatives of methylenebisacrylamide, etc.

The polymerization to make microgels may include the incorporation of initiators for free radical polymerization. Suitable initiators include thermal, Redox and ultraviolet (UV) initiators. Peroxides and aliphatic azo compounds may be used as thermal initiators, and include sodium persulfate, potassium persulfate, ammonium persulfate, benzoyl peroxide (BPO), 2,2-Azobisisobutyronitrile (AIBN), etc. The Redox initiators may consist of oxidants, such as persulfates or hydroperoxides, and reducing agents, such as ascorbic acid, formaldehyde sulfoxilate (SFS), tetramethyl ethylene diamine (TMEDA), a mixture of the disodium salt of 2-hydroxy-2-sulfinatoacetic acid, the disodium salt of 2-hydroxy-2-sulfonatoacetic acid and sodium bisulfite (Bruggolit FF6 and FF7), and sodium metabisulfites, etc. Examples of suitable Redox initiators are ammonium persulfate (APS)/TMEDA, tert-butyl hydroperoxide (TBHP)/FF7, $H_2O_2$/FF7, etc.

The polymerization to make microgels may further include the incorporation of emulsifiers, which include anionic, nonionic, and cationic surfactants, as well as mixtures thereof. Anionic surfactants include sulfonates, sulfates, ether sulfates, phosphate esters. Typical sulfates include ammonium lauryl sulfate, sodium lauryl sulfate (SDS, sodium dodecyl sulfate), linear alcohol exthoxylated and sulphated (Abex 8018), etc. Cationic surfactants may contain primary, secondary, or tertiary amines including dodecyltrimethylammonium bromide (DTAB), cetyltrimethylammonium bromide (CTAB), etc. Short or Long Chain Fatty Alcohols or Alkanes may also be used as co-emulsifiers. Nonionic surfactants include polyoxyethylene such as nonylphenol polyethoxylates (NP-4, NP-9, NP-15, NP-30, NP-40, NP-70, etc), polyoxyethylene glycol, polyoxypropylene glycol, polyoxyethylene glycol sorbitan alkyl esters (polysorbate), sorbitan alkyl esters, etc. Non-surfactant stabilizers such as polyvinyl alcohol and hydroxyethyl cellulose may also be used as interfacial stabilization agents. Mixtures of above surfactants may be used in microgel latex emulsions to ensure the desired colloidal stability.

The organic solvent selection for the aqueous medium in step (b) is dependent on the chemical structure of corrosion inhibitors to be entrapped/immobilized in the microgels. For certain corrosion inhibitors, e.g. benzothiazole and benzotriazole-type compounds, the appropriate solvents should offer good solubility and their boiling point should be lower than 100° C. (boiling point of water) for subsequent solvent striping. In one embodiment, the aqueous medium for dissolving organic corrosion inhibitors such as benzothiazole and benzotriazole-type is a mixture of Isopropyl Alcohol (IPA) and water. However, other similar solvents such as ethanol, methanol or n-propanol may be possible choices as well. For entrapping other corrosion inhibitors that are different from benzotriazole-type compounds in chemical structures, other common solvents with boiling point lower than 100° C., such as Methyl Ethyl Ketone (MEK), acetone, ethyl acetate, etc., may be used, depending on the solubility of the inhibitors.

As the result of step (c) discussed above, some corrosion inhibitor compounds are immobilized or entrapped within the cross-linked polymer network of the microgel particle. Some inhibitor compounds are attached to the cross-linked polymer network by covalent bonding, while other inhibitor compounds are physically entrapped or immobilized within cross-linked polymer network. The core of the microgel particle is relatively hydrophobic while the outer surface of the microgel particle is relatively hydrophilic. The microgel particles produced from step (c) will be referred to as "corrosion-inhibiting microgels" in this disclosure.

The initial microgels, which are produced in step (a), preferably have an average particle size in the range of 50 nm-130 nm. The swollen microgels produced in step (c) may have an average particle size in the range of 160 nm-220 nm, and then after solvent stripping, they shrink to a smaller particle size, such as 130 nm-200 nm.

The average particle size discussed above is determined by a light scattering method and is based on volume average. Dynamic Light Scattering instruments such as Malvern Zetasizer ZS90 or Brookhaven NanoDLS are usually employed for particle size analysis in the nanometer to micron size. Light scattering or laser diffraction particle size analyzers such as Horiba 910, Malvern Mastersizer 2000, Beckman Coulter LS 13 320 are applied for particle size analysis in the submicron to micron size.

Preferably, the latex emulsion produced from step (c) has a solid content of 15%-20% by weight, and after solvent stripping in step (d), the solid content is increased to 20%-30% by weight. Solvent stripping may be carried out by heating at low temperature, e.g. 60° C., under vacuum.

The corrosion-inhibiting microgels resulted from step (d) is in the form of a latex emulsion, which may be incorporated into a primer formulation in this form. Alternatively, the latex emulsion produced from step (d) may be dried off to produce corrosion-inhibiting microgel particles in the form of a powder. The resulting powder may then be added to the primer formulation. The microgel particles in power form may have particle size within the range of 100 nm-10 μm. As an example, the method for obtaining dry microgel particles from latex emulsion may include: (a) using a precipitating agent such as methanol to de-stabilize the latex, (b) collecting the precipitated solids, (c) washing off the surfactants, followed by (d) drying at low temperature to obtain dry powder. As another example, the drying method may include: spray-drying the prepared latex emulsion to obtain dry powder directly (i.e., using nozzle to spray out dried particles at high speed).

By forming microgel particles loaded with corrosion inhibitors in the manner disclosed herein, a high amount of corrosion inhibitors could be incorporated into each particle, e.g. 50-60%. The advantage of such high loading is high efficiency of anti-corrosion performance at reduced charging amount while not affecting other key properties of the primer formulation, into which the corrosion inhibitors are added.

The corrosion-inhibitors entrapped/immobilized in the microgel particles are released in response to a corrosion event, e.g., with a change of pH and/or temperature and/or moisture exposure. When moisture or water permeates through primer film and comes into contact with the microgel particles, the hydrophilic part of polymeric network will be hydrated and swell in volume to allow slow diffusion of inhibitors for release into surrounding area. The temperature and pH increase can facilitate this swelling and accelerate the diffusional release of immobilized inhibitors. In addition, certain specific corrosion inhibitors can also be anchored onto the microgel network through labile chemical bond including ester or amide linkage. The basic hydroxide (pH increase) generated by the corrosion event breaks this chemical linkage and thereby triggers the release of anchored inhibitors into the primer film for corrosion protection. Once released, the active corrosion inhibitors leach to the corrosion site and prevent corrosion of the metal substrate.

Corrosion Inhibitors

Suitable organic corrosion inhibitors for use in the preparation of the corrosion-inhibiting microgel particles may be selected from the following compounds:

a) an amino benzothiazole-based compound having the formula:

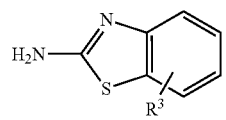

wherein $R^3$ is chosen from H, $C_nH_{2n+1}$, and $OC_nH_{2n+1}$;

b) a benzotriazole-based compound having the formula

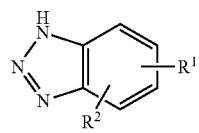

wherein $R^1$ is chosen from H, $C_nH_{2n+1}$, COOH, and OH;
wherein $R^2$ is chosen from H and $C_nH_{2n+1}$;

c) a phenylmaleimide-based compound having the formula:

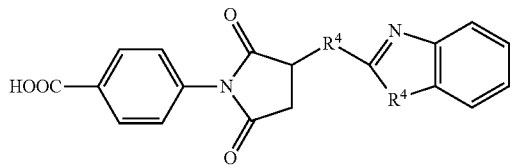

wherein each $R^4$ is independently chosen from: S, NH, and O; and d) a mercaptobenzoimidazole-based compound having the formula:

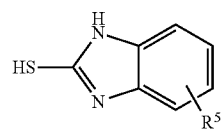

wherein $R^5$ is chosen from: H, $C_nH_{2n+1}$, COOH, and OH; and wherein n is an integer.

As used herein the term "amino benzothiazole-based compound" refers to compounds having a core structure of a benzene ring fused to an amino thiazole ring, such as

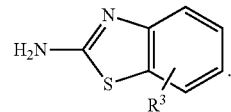

Similarly, as used herein, the term "benzotriazole-based compound" refers to compounds having a core structure of a benzene ring fused to a triazole ring, such as

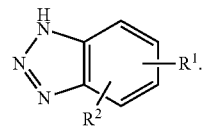

Based on the above, an example of a "carboxybenzotriazole-based compound" would therefore be a compound as depicted above with a carboxyl group as a substituent on the benzene ring.

Examples of organic corrosion inhibitors useful in the compositions and methods described herein include, but are not limited to, amino methyl benzothiazole, thiolated 4-carboxy phenylmaleimide, 4-, and/or 5-carboxybenzotriazole (CBT), and mercaptobenzoimidazole (MBI).

In one embodiment the benzotriazole compound is a carboxybenzotriazole having the following formula:

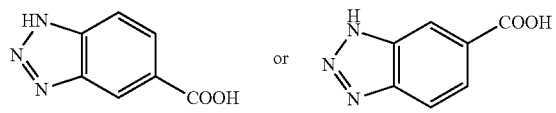 [SMILES: O=C(O)c1ccc2[nH]nnc2c1 ; O=C(O)c1ccc2nn[nH]c2c1]

Another example of a corrosion inhibitor is an aminobenzothiazole-based compound of formula

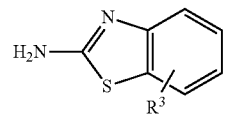

wherein $R^3$ is H, $C_nH_{2n+1}$ or $OC_nH_{2n+1}$; and
wherein n=1-10.

Examples of $C_nH_{2n+1}$ include, but are not limited to, $CH_3$, $C_2H_5$ or $C_3H_7$ and the like. Examples of $OC_nH_{2n+1}$ include, but are not limited to, $OCH_3$, $OC_2H_5$ or $OC_3H_7$ and the like.

In one embodiment, the aminobenzothiazole-based compound is a 2-amino-6-methylbenzothiazole having the following formula:

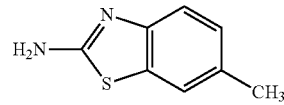

Another example of a corrosion inhibitor is a phenylmaleimide-based compound such as

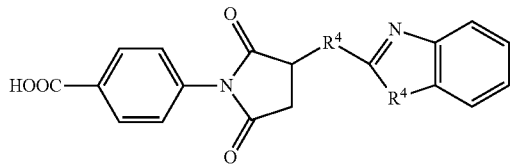

wherein $R^4$ is independently S, NH or O. In one embodiment, each $R^4$ is S, and therefore may be referred to as a thiolated phenylmaleimide.

Non-Chromated Primer Composition

The corrosion-inhibiting microgel particles as discussed above are suitable for incorporation into primer compositions that are to be used in structural bonding. More specifically, the non-chromated primer compositions are suitable for treating metal surfaces prior to metal-to-metal bonding or metal-to-composite bonding. The non-chromated primer composition disclosed herein is capable of achieving corrosion resistance comparable to chromate-containing solutions that have been conventionally used for improving corrosion resistance of highly corrosive substrates such as metals and metal alloys.

The combination of corrosion-inhibiting microgels, the type of curing agents, and the pH of the primer composition as described herein are factors that have been found to affect corrosion performance such that corrosion performance comparable to chromate-containing compositions may be achieved.

The non-chromated primer composition disclosed herein is an aqueous formulation containing: an epoxy resin; a curing agent capable of curing at temperatures greater 200° F. (e.g. 250° F.-350° F.); an organosilane comprising a hydrolysable group; and the corrosion-inhibiting microgels disclosed herein.

The non-chromated (i.e., chromate-free) primer composition disclosed herein offers excellent mechanical and durability properties with most epoxy-based adhesives that are curable at 250° F. and 350° F. Because the chromate-free primer composition has no or very low amount of solvents, it is in compliance with certain governmental safety and health requirements. Furthermore, this primer composition is compatible with various surface treatments such as phosphoric acid anodization and sol-gel surface treatment.

According to one embodiment, the non-chromated primer formulation may comprise an epoxy resin such as ECN 1400 (available from Huntsman) or a combination of epoxy resins including a Novalac epoxy such as Epirez 5003 (available from Huntsman), bisphenol A epoxy such as XU 3903 (available from Resolution Performance products), and DER 669 (available from Dow); a curing agent such as bis(3-aminopropyl)-piperazine ("BAPP") (available from BASF); an organosilane having a hydrolyzable group such as Z-6040 (a gamma-glycidoxypropyltrimethoxy silane available from Dow Corning, Midland, Mich.); and the corrosion inhibiting microgel particles disclosed herein.

The term "chromate" as used herein refers chromate corrosion inhibitors such as strontium chromate, barium chromate, zinc chromate, or calcium chromate. Chromate corrosion inhibitors release hexavalent chromium ($Cr^{6+}$), a human carcinogen, thus, their usage is not desirable.

The term "primer composition" as used herein refers to a composition to be used for structural bonding that provides sufficient adhesion between a metal substrate and a structural adhesive. It also stabilizes the metal oxide layer on the metal substrate and protects metals from corrosion caused, for example, by hot and/or moist and salty environments.

Examples of metal substrates that are suitable for use with non-chromated corrosion inhibiting primer compositions described herein include titanium, aluminum, and alloys thereof, such as Al-2024, Al-6061, Al-7075, or aluminum-lithium alloys.

Epoxy Resins

Suitable epoxy resins for the non-chromated primer composition include conventional solid epoxy resins having functionalities, of at least about 1.8, or at least about 2 functionalities and containing substantially no ionic or ester groups. The epoxy resins are optionally chain-extended, solid glycidyl ethers of phenols, such as resorcinol and the bisphenols, e.g., bisphenol A, bisphenol F, and the like. Also suitable are the solid glycidyl derivatives of aromatic amines and aminophenols, such as N,N,N',N'-tetraglycidyl-4,4'-diaminodiphenylmethane. In other aspects, epoxy resins are solid novolac epoxy resins and solid diglycidyl ether of bisphenol A ("DGEBA") resins. In certain embodiments, the epoxy resins are in a solid form, or produce a solid composition when admixed with other epoxies. In other embodiments, epoxy resins have an epoxy equivalent weight (EEW) of about 145-5000, with an equivalent weight of about 300-750 being preferred, and an equivalent weight of 325 being most preferred. Examples include a Novalac epoxy (such as Epirez 5003 available from Huntsman) and a bisphenol A epoxy (such as XU-3903), or a solid bisphenol A epoxy (such as DER 669) (available from Dow).

Examples of suitable commercial epoxy resins are Epi-Rez® SU-8 (available from Shell Chemical Co.), a polymeric epoxy resin with an average functionality of about 8, melting point (Durran's) of 82° C., and an epoxy equivalent weight (EEW) of 215 available from Shell Chemical Co.; DER 669 (available from Dow), a high molecular weight solid epoxy resin having a Durran's softening point of 135° C. to 155° C. and an epoxy equivalent weight of 3500-5500 available from the Dow Chemical Company; Epi-Rez®, 522-C, a solid DGEBA epoxy having an epoxy equivalent weight of 550-650 and a Durran's melting point of 75° C. to 85° C., available from Shell Chemical Co.; and ECN 1273, 1280, and 1299 Novolac epoxy resins having epoxy functionalities from 3.8 to 5.4, epoxy equivalent weights of from 225 to 235, and melting points of from 73° C. to 99° C., available from Ciba-Geigy. These resins are generally supplied in solid form and ground to a particular particle size, or supplied as an aqueous dispersion. For example, ECN-1299 is available as an aqueous dispersion from Ciba-Geigy as ECN-1440, and Epi-Rez® 522C is available from Shell Chemical Co. as 35201 epoxy dispersion. Epoxy resins are usually present in an amount of about 20-60% by weight based on total weight of the primer composition.

Suitable epoxy co-monomer resins may also be incorporated into the primer composition. Examples of such resins are the bisglycidyl ethers of the bisphenols, particularly bisphenol A, bisphenol F and bisphenol S. Also suitable are the various phenolic and cresolic novolac-type resins, as well as the venous glycidoxy amines and aminophenols, particularly N,N,N',N'-tetrakis(glycidyl)-4,4-diaminodiphenyl methane and N,N,O-tris(glycidyl)-4-aminophenol. Epoxy resins based on the glycidyl ethers of the various dihydroxy-naphthalenes and phenolated dicyclopentadienes are also suitable.

The phenolic resin may include novolac type phenolic resin (the so-called random novolac type phenolic resin)

wherein the ratio of o-methylene to p-methylene bond is less than 1.0 and/or a resole type phenolic resin (methylol type, or dimethylene ether type). Mixtures of the ordinary novolac type phenolic resin and/or the resole type phenolic resin may also be used.

Emulsified epoxies, may be used as co-reactants or modifiers in the primer composition. These emulsions may be added to the primer compositions at 1% to 10% levels. Suitable emulsified epoxies are commercially available from Shell Chemical Co., Ciba-Geigy and Vianova. Some examples include ER 3510-W-60 and ER 3515-W-60 from Shell Chemical Co. or PY 323 from Ciba-Geigy.

In some embodiments, the content of epoxy resin in dispersed phase is from 40% to about 10% by weight, and in the aqueous continuous phase is from 60% to about 90% by weight, of the primer composition. The epoxy resin in dispersed phase may be a dispersion of more than one epoxy resin in the form of a mixture of distinct particles, or may consist of only one type of particles containing more than one epoxy resin per particle. Thus, a flexibilizing epoxy such as the higher molecular weight bisphenol A or bisphenol F epoxies may be blended with a high-temperature resistant epoxy such as TGMDA, then the mixture is cooled, ground, or otherwise dispersed into solid particles of the requisite size. These same epoxy resins might be advantageously dispersed separately without blending.

Mixtures of epoxy resins are also suitable. In one embodiment, the resin mixture contains a solid epoxy resin having a functionality of about 5.5 or less, and a solid epoxy resin having a functionality of about 6 or more. The use of higher functionality epoxy resins, i.e., epoxy resins having a functionality of five or more, in minor amounts is suitable, for examples less than 40 weight percent based on the sum of the weights of all epoxy resins in the composition. The use of such higher functionality epoxy resins in such minor amounts has been unexpectedly found to increase the solvent resistance of the cured primer composition without lowering adhesive properties substantially. A preferred high functionality epoxy resin is Epi-Rez®SU-8, a polymeric solid epoxy resin having an average functionality of eight.

In one embodiment, the non-chromated primer composition includes a mixture of the following epoxy resins:

1) from 30 to 70 weight percent of an epoxy resin having a functionality of from about 1.8 to about 4 and an epoxy equivalent weight of from about 400 to about 800;

2) from 5 to 20 weight percent of an epoxy resin having a functionality of from about 1.8 to about 4 and an epoxy equivalent weight of from about 2000 to about 8000; and 3) from 10 to 40 weight percent of an epoxy resin having a functionality of about 5 or more and having an epoxy equivalent weight of from about 100 to about 400, the weight percents totaling 100 percent based on total weight of the epoxy mixture.

Organosilane

The term "organosilane having a hydrolyzable group" as used herein refers to those organosilanes having a hydrolyzable group.

In one embodiment, the organosilane compound used in the non-chromated corrosion inhibiting primer formulation has silane functional groups that can react or bond to the material to be bonded to a metal surface. In certain embodiments, organsilanes have the following formula:

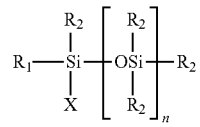

wherein n is greater than or equal to 0; wherein each X is OH, OCH$_3$, and OCH$_2$H$_5$; wherein R$_1$ is CH=CH$_2$,

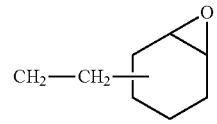

or CH$_2$—CH$_2$—CH$_2$—Y, wherein Y is NH$_2$, SH, OH, NCO, NH—CO—NH$_2$, NH—(CH$_2$)$_3$NH$_2$, NH-Aryl,

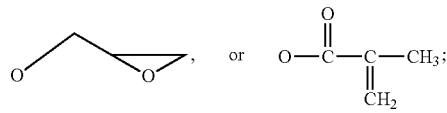

and wherein each R$_2$ is alkyl, alkoxy, aryl, substituted aryl, or R$_1$.

Examples of suitable commercial organosilane compounds available from OSi Specialties Inc., Danbury, Conn. Include, but are not limited to, A-186, a beta-(3,4-epoxycyclo hexyl)ethyltrimethoxy silane; A-187, a gamma-glycidoxypropyltrimethoxysilane; A-189, a gamma-mercaptopropyltrimethoxysilane; A-1100, a gamma-aminopropyltriethoxysilane; A-1106, an aminoalkyl silicone solution; A-1170, a bis-(gamma-trimethoxy-silylpropyl)amine; Y-9669, a N-phenyl-gamma-aminopropyl-trimethoxysilane; Y-11777, an amino alkyl silicone/water solution; and Y-11870, an epoxy functional silane solution. Other suitable commercially available organosilanes include, but are not limited to, Z-6040, a gamma-glycidoxypropyltrimethoxy silane from Dow Corning, Midland, Mich. and HS2759, an aqueous epoxy functional silane; HS2775, an aqueous amino silane solution; and HS2781 an aqueous oligomeric silane solution with amino and vinyl groups all sold by Huls America Inc., Somerset, N.J. Another example is 3-glycidoxypropylmethoxysilane, which is sold under the trademark Z-6040.

Generally, the organosilane is present in the corrosion inhibiting primer composition in amounts ranging from about 0.01 to 75 parts per hundred parts of the epoxy resin, preferably from about 0.01 to 30 parts per hundred parts of the epoxy resin, more preferably from about 0.01 to 10 parts per hundred parts of the epoxy resin and most preferably from about 1 to 7 parts per hundred parts of the epoxy resin.

In some embodiments, the organosilane in liquid form is added directly to the aqueous primer composition. The organosilane is then dispersed in water using a conventional method. For example, one method of dispersing the organosilane in water includes dripping the organosilane into an aqueous solution of thermosetting resin under vigorous stirring. The organosilanes can also be initially dissolved or suspended in a solvent that is miscible with water. In the latter case, the organosilane solution is simply added to the water, without excessive stirring or mixing. The aqueous organosilane solution is then mixed with an aqueous thermosetting composition.

Curing Agent

The curing temperature during structural bonding affects the ability of a primer formulation to achieve the corrosion inhibiting performance of primer compositions when they are used on corrosive substrates, such as aluminum and aluminum alloys. Thus, in a preferred embodiment, the primer formulation contains a curing agent for curing at temperatures greater than 200° F. (93° C.), e.g. 250° F.-350° F. (121-177° C.). In some embodiments, curing agents that can cure at 300° F. (148° C.) or greater may be used.

The "curing agent" for curing epoxy resins as used herein includes substantially water-insoluble curing agents that are solid at room temperature. Examples of such curing agents are aromatic amine curing agents such as 4,4'-diaminodiphenylmethane, 2,2-bis(4-[4-aminophenoxyl]phenyl)propane and 3,3'- and 4,4'-diaminodiphenylsulfone. Further suitable curing agents are 3,3'- and 4,4'-diaminodiphenyloxide, 3,3- and 4,4'-diaminodiphenyloxide, 3,3'- and 4,4'-diaminodiphenylsulfide, and 3,3'- and 4,4'-diaminodiphenylketone. In some embodiments, the curing agent is 4,4'-[1,4-phenylene(1-methylethylidene)]-bis(benzeneamine). Also suitable are the amino and hydroxyl terminated polyarylene oligomers wherein the repeating phenyl groups are separated by ether, sulfide, carbonyl, sulfone, carbonate, or like groups. Examples of such curing agents are the amino- and hydroxyl-terminated polyarylenesulfones, polyaryleneethersulfones, polyetherketones, polyetheretherketones, and like variants.

Also suitable are the amino and hydroxyl terminated polyarylene oligomers wherein the repeating phenyl groups are separated by ether, sulfide, carbonyl, sulfone, carbonate, or like groups. Examples of such curing agents are the amino- and hydroxyl terminated polyarylenesulfones, polyaryleneethersulfones, polyetherketones, polyetheretherketones, and like variants. The curing agents are usually present in amounts from about 2 to about 30 parts per hundred of said thermosetting resin.

Other embodiments of "epoxy curing agents" include a substituted amino triazine such as 2-β-(2'-methylimidazolyl)-1'1-ethyl-4,5-diamino-s-triazine, which is sold under the trademark CUREZOL 2-Mz-Azine®; a modified polyamine sold under the trademark Ancamine 2014®; dicyanadiamide (DICY); imidazoles; bis-urea based curing agents (such as Omicure 24) or Toluene-2,4-bis (N,N'-dimethyl urea) (such as Omicure U-24 from CVC chemicals); amine-epoxy adducts and/or an aromatic amine such as bis(3-aminopropyl)-piperazine (BAPP) (available from BASF).

Other suitable solid diamine curing agents for use with the non-chromated corrosion inhibiting primer formulations of the present invention include 2,4-toluenediamine, 1,4-phenylenediamine, 2,2-bis(4-aminophenyl)hexafluoro propane, 2,2-bis(3-amino-4-hydroxyphenyl)hexafluoro propane, 3,4'-diaminodiphenyloxide, 9,9-bis(4-aminophenyl)fluorene, o-toluidine sulfone, and 4,4'-diaminobenzanilide. Particularly preferred are 9,10-bis(4-aminophenyl)anthracene, 2,2-bis(4-[3-aminophenoxy]phenyl) sulfone, 2,2-bis(4-[4-aminophenoxylphenyl]sulfone, 1,4-bis(4-aminophenoxy) biphenyl, bis(4-[4-aminophenoxy)phenyl)ether, and 2,2-bis ([4-(4-amino-2-trifluorophenoxy)]phenyl) hexafluoropropane. Also included is XU 95101 a curing agent commercially available from Ciba-Geigy. One embodiment of a curing agent is 4,4'-[1,4-phenylene(1-methylethylidene)]-bis(benzeneamine).

In some embodiments, solid amine curing agents having melting points below 240° C., or below 175° C. are utilized. In other embodiments, those solid amine curing agents having melting points below 300° F., or below 220° F. are utilized. When curing agents below 300° F. are used, at least two corrosion inhibitors are required in the primer formulations described herein. In other embodiments, curing agents have a curing temperature of 300° F. or greater, for example, from 300-400° F., 325-375° F., or for example about 350° F., such as BAPP (available from BASF), are used. Curing agents may be used in amounts of about 1-10%, such as about 2-5% total weight of the primer formulation.

The term "corrosion performance" as used herein has its ordinary meaning as known to those skilled in the art and measures the degree of corroded metal after environmental exposure, for example, using image performing software. ASTM B117 is a specification for salt fog exposure, that is, the conditions under which the specimen must be exposed to measure corrosion performance. Specimens exposed under ASTM B117 salt fog may be used to measure corrosion by observation or by using image profiling software that will quantify area that has corrosion based on a picture of the sample. For example, corrosion performance may be measured as percent corrosion after 42 days of salt fog exposure. Corrosion performance that is comparable to chromate means approximately at least 90%, such as at least 95% or 97%, of the specimen is not corroded after exposure. Thus, corrosion performance that is comparable to chromate can mean about less than 10% corrosion, and in other embodiments 5%, 4%, 3%, 2% or less corrosion such as 1%-2%. The specimens may be made using ASTM D1002, a specification for making the samples for performing the corrosion performance testing. ASTM D1002 measures corrosion performance and specifically is a lap shear joint test and measures shear strength of the adhesive joint.

In some embodiments, the non-chromated corrosion inhibiting primer composition has a neutral pH such as 6-8 or 7-8. The releasable corrosion inhibitors incorporated in the microgel particles help to maintain a neutral pH in the primer composition, such as a pH of 6-8 or 7-8, making the primer composition compatible with various surface treatments.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

The term "at least a portion of" as used herein represents an amount of a whole that comprises an amount of the whole that may include the whole. For example, the term "a portion of" may refer to an amount that is greater than 0.01% of, greater than 0.1% of, greater than 1% of, greater than 10% of, greater than 20% of, greater than 30% of, greater than 40% of, greater than 50% of, greater than 60%, greater than 70% of, greater than 80% of, greater than 90% of, greater than 95% of, greater than 99% of, and 100% of the whole.

EXAMPLES

The following examples are provided to assist one skilled in the art to further understand embodiments of the present invention. These examples are intended for illustration purposes and are not to be construed as limiting the scope of the embodiments of the present invention or the claims appended hereto.

Example 1

Preparation of Microgel Corrosion Inhibitor 1

A microgel latex was prepared via emulsion polymerization at 70° C. under nitrogen atmosphere using monomer blend of 75 g ethyl acrylate (EA), 60 g methyl methacrylate (MMA), 105 g methyl methacrylic acid, 30 g diethylene glycol dimethacrylate (EGDMA) and 30 g trimethylolpropane trimethacrylate (TMPTMA), 0.12 g sodium persulfate as initiator, and 30 g abex 8018 as emulsifier. The resulting microgel latex had a solid content of 15%-20% solids by weight and contained microgel particles having average particle size of 50 nm-80 nm.

181 g of an organic inhibitor, 2-amino 6-methylbenzothiazole, was dissolved in an aqueous mixture of isopropanol and water (80/20 ratio) at 50° C. Next, this mixture was added to the microgel latex and stirred for 1 hour. As a result, the microgel particles were swollen into 160 nm-200 nm in size. A microgel inhibitor latex with solid content of 20-30% solids by weight was obtained after de-swelling the particles by stripping off isopropanol at 60° C. under vacuum. The resulting microgel inhibiting microgel particle is being referenced herein as "microgel corrosion inhibitor 1".

A water-based, non-chromated (chromate-free) primer formulation (F1) was prepared according to the formulation disclosed in Table 1. "% wt" refers to percentage by weight.

TABLE 1

Chromate-free Primer Formulation F1

| Components | Amounts |
| --- | --- |
| Non-ionic dispersion of solid Bisphenol A epoxy resin in water | 133 g |
| Aqueous dispersion of epoxidized Bisphenol A novolac resin with an average epoxy functionality of 3 | 72 g |
| Solid reaction product of epichlorohydrin and bisphenol A | 9 g |
| Mixture of aliphatic amines and phenolic resin | 11 g |
| Imidazole curing agent | 4 g |
| Amorphous Silica | 0.3 g |
| Cyanoguanidine (DICY) | 3 g |
| Paliotol Yellow pigment | 1.8 g |
| Microgel corrosion inhibitor 1 | 110 g |
| Glycidoxypropyl trimethoxysilane (Organosilane) | 1% wt of total water content |
| Aqueous solution of Benzisothiazolinone (BIT) | 0.1% wt of total formulation |
| Deionized (DI) water | To provide 25 wt % solids |

The non-chromated primer formulation F1 was sprayed onto FPL-etched aluminum alloy (Al-2024) surface for scribe corrosion test. FPL refers to a surface etching treatment for treating metals according to ASTM D 2651. For comparison, a chromate-based primer formulation BR 6747-1 available from Cytec Industries Inc. (as control) and a chromate-free primer formulation BR 6700-1 available from Cytec Industries Inc. (as a reference) were also sprayed onto FPL-etched aluminum alloy (Al-2024) surfaces for the same scribe corrosion test. BR 6700-1 contains a commercially available, inorganic HALOX® corrosion inhibitor (zinc phosphate-based compound). For mechanical tests, phosphoric acid anodization (PAA) according to ASTM D 3933 was performed after FPL etching. The primer formulations were cured at 250° F. for 1 hr and subjected to three corrosion tests after 1000 hours (42 days) of salt fog exposure (ASTM B 117): a) scribe corrosion test (ASTM D 1654) and b) single lap shear test (ASTM D1002) with an epoxy-based adhesive FM 73 from Cytec Industries Inc., and c) bondline peel with FM 73 adhesive.

The water-based, non-chromated primer formulation F1 provided corrosion performance comparable to chromated primer BR 6747-1 after 1000-hr scribe test, and no obvious corrosion site was found, whereas the non-chromated primer formulation BR 6700-1 using HALOX® inorganic inhibitor showed several corrosion sites close to two scribed lines.

Table 2 shows that the water-based, non-chromated primer formulation F1 provided lap shear strength, before and after salt exposure, that is comparable to chromated primer BR 6747-1 (control), and substantially higher than the non-chromated primer BR 6700-1 using HALOX® inorganic inhibitor. Table 2 also indicates that the water-based primer formulation F1 resulted in bondline peel strength before and after 1000 hour salt exposure that is comparable to chromated primer BR 6747-1 (control), and better than the non-chromated primer BR 6700-1.

TABLE 2

| Inhibitors (° C.) | Average Lap Shear strength Before salt Exposure (psi) | Average Lap Shear strength after 1000 hr Salt exposure (psi) | Average Floating Roller Peel Before salt Exposure (psi) | Average Floating Roller Peel after 1000 hr Salt exposure (psi) |
| --- | --- | --- | --- | --- |
| BR 6747-1 (Chromate-based) | 6372 | 5915 | 64 | 57 |
| BR 6700-1 (Non-chromated) | 5500 | 5250 | 64 | 46 |
| Non-chromated Primer F1 | 6366 | 5492 | 70 | 50 |

Example 2

A water-based, non-chromated primer formulation F2 was prepared according to the formulation disclosed in Table 3. "% wt" refers to percentage by weight.

TABLE 3

Chromate-free Primer Formulation F2

| Components | Amounts |
| --- | --- |
| Non-ionic dispersion of solid Bisphenol A epoxy resin in water | 43 g |
| Aqueous dispersion of epoxidized Bisphenol A novolac resin with an average epoxy functionality of 3 | 23 g |
| Solid reaction product of epichlorohydrin and bisphenol A | 5 g |
| 2,2-Bis-4-(4-aminophenoxy) phenyl propane | 10 g |
| Toluene-2,4-bis (N,N'-dimethyl urea) | 4 g |
| Paliotol Yellow | 1 g |
| Microgel corrosion inhibitor 1 | 65 g |
| Amorphous silica (Cabosil) | 0.2 g |
| Glycidoxypropyl trimethoxysilane (Organosilane) | 1% wt of total water content |
| Aqueous solution of Benzisothiazolinone (BIT) | 0.1 wt of total formulation |
| DI water | To provide 20 wt % solids |

The above formulation F2 and chromated primer formulation BR 6747-1 (control) were sprayed onto FPL etched surface of Al-2024 aluminum alloy for scribe corrosion tests. For mechanical tests, phosphoric acid anodization was performed after FPL etching. The primer formulations were cured at 250° F. for 1 hr and subjected to three corrosion tests after 1000 hours (42 days) of salt fog exposure (ASTM B 117): a) scribe corrosion test (ASTM D 1654) and b) bondline peel with FM 73 adhesive. The non-chromated primer formulation F2 using microgel inhibitor resulted in 1000-hr scribe corrosion performance comparable to chromated primer BR 6747-1.

Example 3

Preparation of Microgel Corrosion Inhibitor 2

Microgel latex was prepared via emulsion polymerization at 70° C. under nitrogen atmosphere using a monomer blend of 75 g ethyl acrylate (EA), 60 g methyl methacrylate (MMA), 105 g methyl methacrylic acid, 30 g diethylene glycol dimethacrylate (EGDMA) and 30 g trimethylolpropane trimethacrylate (TMPTMA), 0.12 g sodium persulfate as initiator, and 30 g abex 8018 as emulsifier. The resulting microgel latex had a solid content of 15-20% solids and microgel particles having average particle size of 50 nm-80 nm.

Organic inhibitor carboxy benzotriazole of 180 g is dissolved in isopropanol and water mixture of 80/20 ratio at 50° C. Then this mixture is added to the microgel nanolatx and stirred for 1 hour. The latex particles are swollen into 160 nm-200 nm in size. The microgel inhibitor latex with 20-30% wt solids is obtained after de-swell the particles by stripping off isopropanol at 60° C. under vacuum. The resulting microgel inhibiting microgel particle is being referenced herein as "microgel corrosion inhibitor 2".

A water-based, non-chromated primer formulation F3 was prepared according to the formulation disclosed in Table 4. "% wt" refers to percentage by weight.

TABLE 4

Non-chromated Formulation F3

| Components | Amount |
| --- | --- |
| Non-ionic dispersion of solid Bisphenol A epoxy resin in water | 133 g |
| Aqueous dispersion of epoxidized Bisphenol A novolac resin with an average epoxy functionality of 3 | 72 g |
| Solid reaction product of epichlorohydrin and bisphenol A | 9 g |
| Amine curing agent (mixture of aliphatic amines and phenolic resin) | 11 g |
| Imidazole curing agent | 4 g |
| Amorphous silica | 0.3 g |
| Cyanoguanidine (DICY) | 3 g |
| Paliotol Yellow pigment | 1.8 g |
| Microgel corrosion inhibitor 2 | 110 g |
| Glycidoxypropyl trimethoxysilane (Organosilane) | 1% wt of total water content |
| Aqueous solution of Benzisothiazolinone (BIT) | 0.1% wt of total formulation |
| DI water | To provide 25 wt % solids |

The above shown formulation and chromated primer BR 6747-1 control were sprayed onto FPL etched Al-2024 alloy for scribe corrosion tests. For mechanical tests, phosphoric acid anodizing was performed after FPL etching. The primers were cured at 250° F. for 1 hr and subjected to three corrosion tests after 1000 hours (42 days) of salt fog exposure (ASTM B 117): a) scribe corrosion test (ASTM D 1654) and b) bondline peel with FM 73 adhesive. The novel non-chromated primer formulation F3 using microgel corrosion inhibitor 2 showed 1000-hr scribe corrosion performance comparable to chromated primer BR 6747-1.

Example 4

A water-based, non-chromated primer formulation F4 was prepared according to the formulation disclosed in Table 5. "% wt" refers to percentage by weight.

TABLE 5

Non-chromated Primer Formulation F4

| Components | Amounts |
| --- | --- |
| Epoxy Cresol Novolac Resin | 50 g |
| 2,2-Bis-4-(4-aminophenoxy) phenyl propane | 19 g |
| Paliotol Yellow pigment | 0.45 g |
| Amorphous Silica | 0.2 g |
| Microgel corrosion inhibitor 1 | 125 g |
| Glycidoxypropyl trimethoxysilane (Organosilane) | 0.25 wt % of total water content |
| Aqueous solution of Benzisothiazolinone (BIT) | 0.1 wt % of total formulation |
| DI water | To provide 20 wt % solids |

The above primer formulation F4 and chromate-based primer formulation BR 6750 available from Cytec Industries Inc. (as control) were sprayed onto FPL etched Al-2024 aluminum alloy surface for scribe corrosion tests. For mechanical tests, phosphoric acid anodization was performed after FPL etching. The primer formulations were cured at 350° F. for 1 hr and subjected to three corrosion tests after 1000 hours (42 days) of salt fog exposure (ASTM B 117): a) scribe corrosion test (ASTM D 1654) and b) bondline peel with FM 350NA adhesive. The novel non-chromated primer formulation F4 using microgel corrosion inhibitor 1 showed comparable 1000-hr scribe corrosion performance as chromate-based primer formulation BR 6750.

Example 5

Comparative Primer Formulation with Pure Benzothiazole

For comparison, a primer formulation was prepared according to the Formulation P1 disclosed in Table 6. "% wt" refers to percentage by weight.

TABLE 6

| Formulation P1 | |
| --- | --- |
| Components | Amount |
| Non-ionic dispersion of solid Bisphenol A epoxy resin in water | 738 g |
| Polymer of epoxy resin & bisphenol A | 95.6 g |
| A high molecular weight solid reaction product of epichlorohydrin and bisphenol A | 121.7 g |
| BAPP | 92 g |
| Amine curing agent (Omnicure 24) | 27 g |
| Paliotol Yellow pigment | 7.3 g |
| Amorphous silica | 16 g |
| DI water | To provide 57% wt solids |

Subsequently, 150 g of the primer Formulation P1 was combined with 12.6 g of HALOX Z-PLEX 111 (a zinc phosphate-based corrosion inhibitor), 25.2 g of pure 2-amino 6-methylbenzothiazole (without microgel encapsulation), and 414 g of DI water to form a corrosion inhibiting primer formulation.

After overnight storage at ambient condition, it was observed that big blocks of solid clumps formed in the prepared primer formulation and could not be re-dispersed, indicating that direct addition of pure 2-amino 6-methylbenzothiazole caused the formulation to lose its stability. In contrast, the formulations containing microgel corrosion inhibitors 1 and 2 (Formulations F1-F4) maintained its colloidal stability after long term storage, over one month at ambient condition.

What is claimed is:

1. A discrete, corrosion-inhibiting microgel comprising:
a cross-linked polymer network created by emulsion polymerization of monomers selected from: mono-functional or bi-functional acrylic monomers; mono-functional or bi-functional methacrylic monomers; mono-functional vinyl monomers, and combinations thereof; and
organic corrosion-inhibiting compounds entrapped or immobilized within the polymer network,
wherein emulsion polymerization is carried out in the presence of an initiator for free radical polymerization and cross-linking monomers selected from: diacrylates; dimethacrylates; triacrylates; trimethacrylates; dipentaerythritol pentaacrylate; pentaerythritol tetraacrylate; derivatives of methylenebisacrylamide; and combinations thereof,
wherein the corrosion-inhibiting compounds are releasable from the polymer network upon exposure to a corrosion-triggering condition selected from: pH change, moisture exposure, temperature increase, and combination thereof.

2. The microgel of claim 1, wherein the corrosion-inhibiting compounds are selected from the following:
(a) amino benzothiazole-based compounds having the formula:

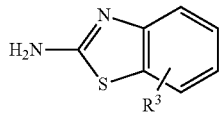

wherein $R^3$ is chosen from H, $C_nH_{2n+1}$ and $OC_nH_{2n+1}$;
(b) benzotriazole-based compounds having the formula

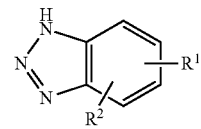

wherein $R^1$ is chosen from H, $C_nH_{2n+1}$, COOH, and OH;
wherein $R^2$ is chosen from H and $C_nH_{2n+1}$;
(c) phenylmaleimide-based compounds having the formula:

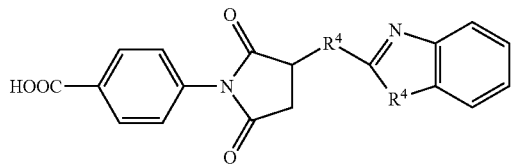

wherein each $R^4$ is independently chosen from: S, NH, and O; and
(d) mercaptobenzoimidazole-based compounds having the formula:

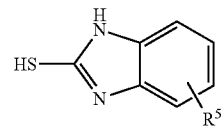

wherein $R^5$ is chosen from: H, $C_nH_{2n+1}$, COOH, and OH; and n is an integer.

3. The microgel of claim 1, wherein the initiator for free radical polymerization is selected from: peroxides; hydroperoxides; persulfates; aliphatic azo compounds; ascorbic acid; formaldehyde sulfoxilate (SFS); tetramethyl ethylene diamine (TMEDA); sodium metabisulfite; and a mixture of disodium salt of 2-hydroxy-2-sulfinatoacetic acid, disodium salt of 2-hydroxy-2-sulfonatoacetic acid and sodium bisulfate.

4. The microgel of claim 1, wherein some corrosion-inhibiting compounds are covalently bonded to the cross-linked polymer network and some corrosion-inhibiting compounds are physically entrapped or immobilized within the network.

5. A chromate-free, corrosion inhibiting primer composition comprising:
at least one epoxy resin;
a curing agent;
an organosilane comprising a hydrolysable group; and
the corrosion-inhibiting microgel of claim 1.

6. The primer composition of claim 5, wherein the curing agent is an amine compound selected from: aromatic amines; substituted amino triazine; modified polyamine;

dicyanadiamide (DICY); bis-urea based curing agents; amine-epoxy adducts; diamines, imidazoles; and combinations thereof.

7. The primer composition of claim 6, wherein the amine curing agent is an aromatic amine selected from: bis(3-aminopropyl)-piperazine (BAPP); 4,4'-diaminodiphenylmethane; 2,2-bis(4-[4-aminophenoxy]phenyl)propane; 3,3'- and 4,4'-diaminodiphenylsulfone; amino and hydroxyl terminated polyarylene oligomers wherein the repeating phenyl groups are separated by one of ether, sulfide, carbonyl, sulfone, and carbonate groups.

8. The primer composition according to claim 6, wherein the amine curing agent is selected from: 9,10-bis(4-aminophenyl)anthracene; 2,2-bis(4-[3-aminophenoxy]phenyl) sulfone; 2,2-bis(4-[4-aminophenoxy]phenyl) sulfone; 1,4-bis (4-aminophenoxy)biphenyl; bis(4-[4-aminophenoxy) phenyl) ether; 2,2-bis([4-(4-amino-2-trifluorophenoxy)] phenyl) hexafluoropropane; 4,4'-[1,4-phenylene(1-methylethylidene)]-bis(benzeneamine).

9. A method for forming corrosion-inhibiting microgels, said method comprising:
a) forming discrete microgels by emulsion polymerization of monomers selected from: mono-functional or bi-functional acrylic monomers; mono-functional or bi-functional methacrylic monomers; mono-functional vinyl monomers, and combinations thereof;
b) dissolving an organic corrosion inhibitor in an aqueous medium containing an organic solvent and water;
c) mixing the microgels with the aqueous medium, causing the microgels to swell and the organic corrosion inhibitor compounds to become entrapped or immobilized within the polymer networks; and
d) stripping off the solvent to produce a latex emulsion with microgels of smaller particle sizes,
wherein emulsion polymerization at (a) is carried out in the presence of an initiator for free radical polymerization and cross-linking monomers selected from: diacrylates; dimethacrylates; triacrylates; trimethacrylates; dipentaerythritol pentaacrylate; pentaerythritol tetraacrylate; derivatives of methylenebisacrylamide; and combinations thereof.

10. The method of claim 9, wherein the initiator for free radical polymerization is selected from: peroxides; hydroperoxides; aliphatic azo compounds; persulfates; ascorbic acid; formaldehyde sulfoxilate (SFS); tetramethyl ethylene diamine (TMEDA); sodium metabisulfite; and a mixture of disodium salt of 2-hydroxy-2-sulfinatoacetic acid, disodium salt of 2-hydroxy-2-sulfonatoacetic acid, and sodium bisulfite.

11. The method of claim 9, wherein the organic corrosion inhibitor used in step (b) is selected from:
(i) amino benzothiazole-based compounds having the formula:

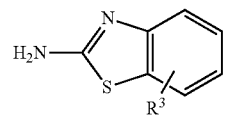

wherein $R^3$ is chosen from H, $C_nH_{2n+1}$ and $OC_nH_{2n+1}$;
(ii) benzotriazole-based compounds having the formula

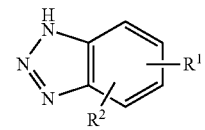

wherein $R^1$ is chosen from H, $C_nH_{2n+1}$, COOH, and OH; wherein $R^2$ is chosen from H and $C_nH_{2n+1}$;
(iii) phenylmaleimide-based compounds having the formula:

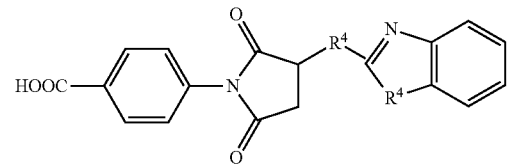

wherein each $R^4$ is independently chosen from: S, NH, and O; and
(iv) mercaptobenzoimidazole-based compounds having the formula:

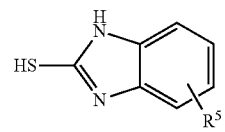

wherein $R^5$ is chosen from: $H_nCH_{2n+1}$, COOH, and OH; and n is an integer.

12. The method of claim 9, further comprising spraying-drying the latex emulsion resulted from step (d) to produce microgel particles in a powder form.

13. Corrosion-inhibiting particles in powder form produced by the method of claim 12.

14. The method of claim 9, further comprising destabilizing and drying the latex emulsion resulted from step (d) to produce microgel particles in a powder form.

15. Corrosion-inhibiting microgels produced by the method of claim 9.

* * * * *